United States Patent
Jugl et al.

(10) Patent No.: US 10,420,890 B2
(45) Date of Patent: Sep. 24, 2019

(54) ASSEMBLY FOR A DRUG DELIVERY DEVICE AND USE OF AN ATTENUATION MEMBER

(71) Applicant: Sanofi-Aventis Deutschland GMBH, Frankfurt am Main (DE)

(72) Inventors: Michael Jugl, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 337 days.

(21) Appl. No.: 14/913,188

(22) PCT Filed: Aug. 15, 2014

(86) PCT No.: PCT/EP2014/067469
§ 371 (c)(1),
(2) Date: Feb. 19, 2016

(87) PCT Pub. No.: WO2015/024872
PCT Pub. Date: Feb. 26, 2015

(65) Prior Publication Data
US 2016/0199585 A1    Jul. 14, 2016

(30) Foreign Application Priority Data
Aug. 22, 2013   (EP) .................................... 13181273

(51) Int. Cl.
*A61M 5/315* (2006.01)
*A61M 5/24* (2006.01)

(52) U.S. Cl.
CPC ........... *A61M 5/31511* (2013.01); *A61M 5/24* (2013.01); *A61M 5/3157* (2013.01);
(Continued)

(58) Field of Classification Search
CPC .. A61M 2005/2086; A61M 2005/2418; A61M 2005/3143; A61M 2005/3152;
(Continued)

(56) References Cited

U.S. PATENT DOCUMENTS

| 533,575 A | 2/1895 | Wilkens |
| 3,825,003 A | 7/1974 | Kruck |

(Continued)

FOREIGN PATENT DOCUMENTS

| EP | 0937471 A2 | 8/1999 |
| EP | 0937476 A2 | 8/1999 |

(Continued)

OTHER PUBLICATIONS

International Search Report and Written Opinion in International Application No. PCT/EP2014/067469, dated Oct. 29, 2014, 8 pages.
(Continued)

*Primary Examiner* — Kevin C Sirmons
*Assistant Examiner* — Tezita Z Watts
(74) *Attorney, Agent, or Firm* — Fish & Richardson P.C.

(57) ABSTRACT

An assembly for a drug delivery device includes a first member and an attenuation member. The first member includes a main body and an elastically displaceable feature connected to the main body. The attenuation member mechanically cooperates with the elastically displaceable feature to influence the force which has to be exerted on the elastically displaceable feature to displace the elastically displaceable feature elastically with respect to the main body. An attenuation member can be used in a drug delivery device to tune the force required to elastically displace an elastically displaceable feature of a first member of the drug delivery device by bringing the attenuation member into mechanical cooperation with the elastically displaceable feature.

19 Claims, 3 Drawing Sheets (52) U.S. Cl.
CPC ..... *A61M 5/31535* (2013.01); *A61M 2205/43* (2013.01); *A61M 2205/581* (2013.01); *A61M 2205/582* (2013.01)

(58) Field of Classification Search
CPC ........ A61M 2205/581; A51M 5/31511; A51M 5/315; A51M 5/31541; A51M 5/24
See application file for complete search history.

(56) References Cited

U.S. PATENT DOCUMENTS

| | | |
|---|---|---|
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,687 B1 | 2/2001 | Lo |
| 6,193,698 B1 | 2/2001 | Kirchhofer et al. |
| 6,221,046 B1 * | 4/2001 | Burroughs ........ A61M 5/31551 604/153 |
| 6,235,004 B1 | 5/2001 | Steenfeldt-Jensen et al. |
| 6,248,093 B1 * | 6/2001 | Moberg ............. A61M 5/1456 128/DIG. 12 |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 8,277,415 B2 * | 10/2012 | Mounce ................ A61J 1/1406 604/150 |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0038394 A1 | 2/2005 | Schwarzbich |
| 2005/0113765 A1 | 5/2005 | Veasey et al. |
| 2006/0153693 A1 | 7/2006 | Fiechter et al. |
| 2009/0275916 A1 | 11/2009 | Harms et al. |
| 2010/0016794 A1 * | 1/2010 | Corrigan ............. A61M 5/2033 604/134 |
| 2010/0094205 A1 * | 4/2010 | Boyd ................. A61M 5/31595 604/68 |
| 2010/0137798 A1 * | 6/2010 | Streit ................. A61M 5/2033 604/110 |
| 2011/0046565 A1 * | 2/2011 | Radmer ................ A61M 5/20 604/211 |
| 2011/0054414 A1 * | 3/2011 | Shang ................ A61M 5/2033 604/218 |
| 2016/0074584 A1 * | 3/2016 | Carmel .................. A61M 5/24 604/197 |

FOREIGN PATENT DOCUMENTS

| | | | |
|---|---|---|---|
| EP | 2399631 A1 * | 12/2011 | .......... A61M 5/2033 |
| EP | 2399631 A1 * | 12/2011 | .......... A61M 5/2033 |
| EP | 2515976 | 10/2012 | |
| GB | 2438591 | 12/2007 | |
| JP | 3077929 | 6/2001 | |
| JP | 2010-509956 | 4/2010 | |
| WO | 9938554 A1 | 8/1999 | |
| WO | 0110484 A1 | 2/2001 | |
| WO | WO2008/058665 | 5/2008 | |
| WO | WO 2011/075760 | 6/2011 | |

OTHER PUBLICATIONS

International Preliminary Report on Patentability in International Application No. PCT/EP2014/067469.
Rote Liste, "50. Hypophysen-, Hypothalamushormone, andere regulatorische Peptide u. ihre Hemmstoffe," Chapter 50, ed. 2008, 20 pages.

* cited by examiner

ASSEMBLY FOR A DRUG DELIVERY DEVICE AND USE OF AN ATTENUATION MEMBER

CROSS-REFERENCE TO RELATED APPLICATIONS

This application is a U.S. national stage application under 35 USC § 371 of International Application No. PCT/EP2014/067469, filed on Aug. 15, 2014, which claims priority to European Patent Application No. 13181273.7, filed on Aug. 22, 2013, the entire contents of which are incorporated herein by reference.

TECHNICAL FIELD

The present disclosure relates to an assembly for a drug delivery device, preferably a mechanically operated device, and to the use of an attenuation member.

BACKGROUND

In drug delivery devices, usually audible and/or tactile feedbacks are generated during operation so as to provide to the user indicating that the device performs the desired function. In mechanically operated, non-electrically driven, devices the feedback is usually generated by mechanical interaction of components of the device. Such feedbacks include end-of-dose dispense feedbacks in drug delivery devices for dispensing a dose of drug, for example an audible click which indicates that the dispensing action has been completed. Likewise, the feedbacks often include a dose set feedback which indicates that a dose of drug which is dispensed later on by the device has been set for being dispensed. The respective feedback increases the user's confidence that the device functions properly.

SUMMARY

It is an object of the present disclosure to facilitate provision of a novel, preferably an improved, drug delivery device.

This object is achieved by the subject-matter of the independent claims. Advantageous embodiments and refinements are subject-matter of dependent claims.

One aspect of the disclosure relates to an assembly for a drug delivery device. Another aspect relates to a feedback mechanism with the assembly, a feedback mechanism for the assembly or for the drug delivery device. A further aspect relates to a drug delivery device which comprises the assembly. Yet another aspect relates to the use of an attenuation member in the drug delivery device or in the assembly.

Features described below with respect to the assembly, the feedback mechanism, the drug delivery device or the use of the attenuation member therefore are also disclosed herein with respect to the other aspects, even if the respective feature is not explicitly mentioned in the context of the relevant aspect. For example, features described in conjunction with the use of the attenuation member or the drug delivery device are also disclosed for the feedback mechanism or the assembly and vice versa.

In an embodiment, the drug delivery device is a portable device. The device may be an injection device. The device may be a pen-type device. The device may be a device which is used for self-administration by the user. The device may be designed to be used by persons without formal medical training, e.g. by patients.

In an embodiment, the assembly comprises a first member. The first member comprises a main body and an elastically displaceable feature, which is preferably connected to the main body. The feature may be elastically displaceable with respect to the main body. The elastically displaceable feature may be formed integrally with or resiliently mounted to the main body.

In an embodiment, the assembly comprises an attenuation member. The attenuation member may mechanically cooperate with, preferably abut, the elastically displaceable feature. The attenuation member may be provided to influence the force, preferably to increase the force, which has to be exerted on the elastically displaceable feature to displace the elastically displaceable feature elastically with respect to the main body. Particularly, in the assembly or in the drug delivery device, influencing the force required for elastic displacement of the feature may be the sole purpose of the attenuation member. Thus, the drug delivery device may work also without the attenuation member and, particularly, perform all the functions it is designed for without the attenuation member. The attenuation member may be an add-on which is used to tune the force required for displacement in a fully operable drug delivery device.

Providing an attenuation member has particular advantages. For example, depending on what kind of attenuation member is provided, the forces to displace the elastically displaceable feature can be tuned. Thus, the device may be customized for different users by means of different attenuation members. Particularly, for physically stronger users attenuation members may be used which increase the force required to displace the elastically displaceable feature considerably, whereas, for physically weaker persons, attenuation members may be applied which do not increase the force considerably.

In an embodiment, the elastically displaceable feature is arranged to be displaced elastically from an undisplaced position to a displaced position during operation of the assembly or the drug delivery device, such as during a dose setting operation and/or a dose dispensing operation. During the displacement towards the displaced position, the attenuation member may be in permanent mechanical contact with the elastically displaceable feature. The elastically displaceable feature is preferably provided to be displaced from the displaced position towards and/or back into the undisplaced position by an elastic restoring force, preferably during operation of the assembly or the drug delivery device, particularly at an end of the dose setting and/or the dose dispensing operation. During one of these movements, preferably during the movement towards the undisplaced position, or at the end of this movement, a feedback can be generated, for example by the elastically displaceable feature hitting a solid member of the assembly, thus producing a clicking or snapping sound. Thus, by providing the attenuator, audible and/or tactile feedbacks, such as click or snap noises, occurring during operation of a drug delivery device can be varied or tuned. The feedback generated may be customized for different users by providing different attenuation members, which preferably influence the force required for displacement and/or the elastic restoring force in a different way.

In an embodiment, the attenuation member is used to tune the force required to elastically displace the elastically displaceable feature of the first member of the assembly or the drug delivery device. For example, the tuning may be performed by bringing the attenuation member into mechanical cooperation with the elastically displaceable feature.

In an embodiment, the attenuation member is provided to adjust an audible and/or tactile feedback. The feedback may be generatable when the elastically displaceable feature, after having been displaced, particularly to the displaced position, moves towards its undisplaced position or reaches the undisplaced position, for example by cooperation of a surface of the feature with a surface of a different element or member, e.g. the second member described further below, of the drug delivery device or the assembly as set forth further above and below.

Additionally or alternatively to tuning the force and/or the feedback, the attenuation member may be provided to absorb forces acting on the device or the assembly from the outside, such as vibrational forces occurring when the device is carried by the user or dropped on the floor, for example. Consequently, the attenuation member may be used to prevent an unintended displacement of the elastically displaceable feature, which may cause a malfunction of the device. Thus, user safety of the device is increased by the attenuation member.

In an embodiment, the respective elastically displaceable feature is a finger extending in the axial direction.

In an embodiment, the elastically displaceable feature is deformable, preferably elastically deformable. On account of the elastic deformation, a resilient mounting of the feature to the main body may be dispensed with and an integral formation is facilitated. The feature may be a flexible feature. Flexibility of the feature as compared to the main body may be provided by a two cut-outs, particularly within the main body, which delimit the feature in two, preferably circumferential and/or opposite, directions.

In an embodiment, the attenuation member is deformable, preferably elastically deformable. Due to the mechanical cooperation of attenuation member and elastically displaceable feature, the force required to elastically displace the elastically displaceable feature from the undisplaced position into the displaced position has contributions from a force required to elastically displace the feature and from a force required to deform the attenuation member. Thus, the force required to elastically displace the feature may be increased compared to a situation where no attenuation member is present. If the attenuation member is elastically deformable, the restoring force may comprise contributions of the restoring force resulting from displacement of the elastically displaceable feature and from the deformation of the attenuation member.

During movement from the displaced position to the undisplaced position, depending on the restoring forces for the attenuation member and the elastically displaceable feature, the attenuation member and the elastically displaceable feature may be out of contact for a certain amount of time, for example, if the restoring force provided by the elastically displaceable feature is less than the one provided by the attenuation member. However, expediently, the attenuation member is configured such that the elastic restoring force which tends to return the attenuation member into an undeformed state is greater than the elastic restoring force provided by the elastically displaceable feature. Thereby, it is ensured that the attenuation member and the elastically displaceable feature are kept in permanent contact also on the way from the displaced position towards the undisplaced position. In this way, the forces as well as the audible and/or tactile feedback can be tuned reliably.

Particularly, the attenuation member may be elastically deformed when the elastically displaceable feature is displaced. The attenuation member is expediently chosen such that the elastic restoring force tending to restore the undeformed shape of the attenuation member is greater than the elastic restoring force provided by the elastic displacement of the elastically displaceable feature, e.g. the force which tends to move the displaceable feature towards the undisplaced position due to the elastic displacement of the elastically displaceable feature.

In an embodiment, the attenuation member is in permanent mechanical contact with the the elastically displaceable feature, particularly when the feature is in the displaced and/or undisplaced position.

In an embodiment, the attenuation member is arranged between the elastically displaceable feature and a counter-bearing such that the elastically displaceable feature and the attenuation member are kept in, preferably permanent, mechanical contact, particularly when the elastically displaceable feature is in the displaced and/or in the undisplaced position.

In an embodiment, the assembly comprises a plurality of elastically displaceable features. The attenuation member may be in, preferably permanent, mechanical, contact with a plurality of, preferably with all of, the elastically displaceable features, particularly when the respective feature is in the undisplaced and/or displaced position.

In an embodiment, the attenuation member is clamped between at least two and/or between all of the elastically displaceable features.

In an embodiment, the attenuation member may be secured to the first member. Particularly, the attenuation member may be received within the first member.

In an embodiment, the assembly comprises a second member. The second member may be movably coupled to the first member. The second member may be movable with respect to the first member during operation of the drug delivery device. The first member and/or the second member may be part of a dose setting and/or drive mechanism which is designed for setting and/or dispensing a dose of drug when implemented within a drug delivery device. Relative movement of the second member with respect to the first member may be converted into movement of the elastically displaceable feature from the undisplaced position to the displaced position. For example, the relative movement may be a dose setting movement or a dose dispensing movement. The moved member may be the second member whereas the first member may be held stationary. The second member may be moved from a first position, e.g. an unset position, to a second position, e.g. a dose set position, with respect to the first member. During this movement, the elastically displaceable feature may be elastically displaced and, once the second position has been reached, or shortly before the second position has been reached, the elastically displaceable feature may be moved back towards the undisplaced position. Thereby, preferably an audible and/or tactile feedback is created, e.g. by the elastically displaceable feature hitting the second member.

In an embodiment, the elastically displaceable feature is arranged to be displaced or displaced in the radial direction, particularly when the first member is moved axially with respect to the second member or when the second member is moved axially with respect to the first member. The first member may have or may define a longitudinal direction, e.g. a main longitudinal direction. The elastically displaceable feature may be arranged to be elastically displaced in the radial direction with respect to the longitudinal direction and/or with respect to the axial direction of the relative movement between first member and second member.

In an embodiment, the second member comprises a protruding feature, e.g. a section of a thread or defining a thread.

The thread may be provided on the second member provided on the second member. The protruding feature may be arranged to mechanically cooperate with the elastically displaceable feature to displace this feature when the first member is moved with respect to the second member or vice versa.

In an embodiment, the assembly is configured such that the elastically displaceable feature is displaced from the undisplaced position to the displaced position when the protruding feature cooperates with, preferably abuts, the elastically displaceable feature. Expediently, the elastically displaceable feature remains displaced as long as the protruding feature mechanically cooperates with the elastically displaceable feature. When the protruding feature has passed the elastically displaceable feature or vice versa, there is no longer mechanical cooperation of protruding feature and elastically displaceable feature and the elastically displaceable feature is, on account of the elastic restoring force, movable or moved towards the undisplaced position. The elastic restoring force is expediently influenced, e.g. increased, by the attenuation member.

In an embodiment, the second member is designed to transfer a driving force to the first member, preferably by mechanical cooperation of the protruding feature and the elastically displaceable feature. The driving force may be an axial force. The displacement force required to displace the elastically displaceable feature may be a radial force, particularly perpendicular to the driving force. Thus, the second member may be a drive member to drive movement of the first member in the drug delivery device or the assembly. The second member may be a drive sleeve. The elastically displaceable feature may be retained within the drive member. The elastically displaceable feature may be in mechanical contact with an inner surface of the drive member.

In an embodiment, the second member, in particular an inner surface thereof, is provided with a thread. The thread or a section thereof may be provided to interact with the (respective) elastically displaceable feature, preferably to transfer the driving force to the first member and/or to displace the elastically displaceable feature. The protruding feature may be a section of the thread of the second member or may define the thread of the second member.

In an embodiment, the first member is a piston rod. The first member may be a lead screw or a toothed rod, for example. The piston rod may be designed to transfer the driving force to a bung within a cartridge of the drug delivery device to dispense drug from the cartridge when the device is operated.

In an embodiment, the first member comprises a first section configured to establish a threaded engagement of a first lead. The first section may be configured to establish the threaded engagement with the thread of the second member. The lead of the threaded engagement may be defined by the lead of the thread of the second member. The (respective) elastically displaceable feature may be arranged in the first section and, particularly, may be provided to establish the threaded engagement. Thus, the elastically displaceable feature(s) may cooperate with the thread of the second member to establish the threaded engagement of the first lead.

In an embodiment, the first member, preferably the main body, comprises a second section to establish a threaded engagement of a second lead. The second lead is expediently different from the first lead. By means of the differences between the first and second lead a mechanical advantage can be achieved. The thread defining the lead of the threaded engagement may be a thread provided on the main body. In the drug delivery device the thread on the main body may cooperate with a nut member. Consequently, when the second member transfers a driving force to the first member, the first member may rotate and, on account of the threaded engagement, be axially displaced with respect to the nut member. Thus, the first member may be used to advance a piston or bung within a cartridge of the drug delivery device.

In a particularly advantageous embodiment, an assembly is provided comprising:
 a first member comprising a main body and an elastically displaceable feature connected to the main body,
 an attenuation member, wherein
the attenuation member mechanically cooperates with, preferably abuts, the elastically displaceable feature to influence the force which has to be exerted on the elastically displaceable feature to displace the elastically displaceable feature elastically with respect to the main body.

A further particularly advantageous embodiment relates to the use of an attenuation member in a drug delivery device to tune the force required to elastically displace an elastically displaceable feature of a first member of the drug delivery device by bringing the attenuation member into mechanical cooperation with the elastically displaceable feature.

As can be seen from the disclosure above, these embodiments have various advantages.

Further features, advantageous embodiments and expediencies are disclosed in the following description of the exemplary embodiment in conjunction with the figures.

BRIEF DESCRIPTION OF THE DRAWINGS

Like elements, elements of the same kind and identically acting elements are provided with corresponding reference numerals.

DETAILED DESCRIPTION

Figure 1:
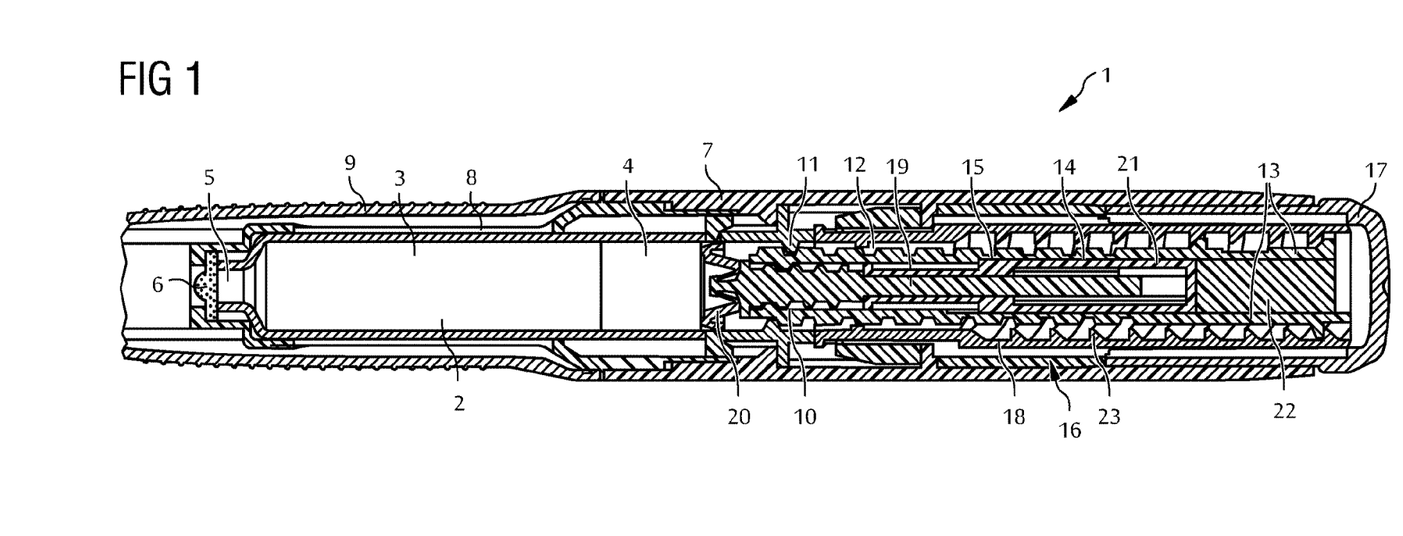
FIG. 1 shows an exemplary embodiment of a drug delivery device on the basis of a schematic sectional view.

FIG. 1 shows, on the basis of a schematic sectional view, an exemplary embodiment of a drug delivery device 1. The drug delivery device 1 may be an injection device. The drug delivery device 1 may be a pen-type device. The drug delivery device 1 may be a disposable or a reusable device. The drug delivery device 1 may be a fixed dose device. Alternatively, the present concept is also applicable for variable dose devices where the size of the dose to be set can be varied by the user, whereas in fixed dose devices the size of the dose may not be varied by the user but is preset by the device design.

It should be noted that the above-mentioned concept with the attenuation member should not be construed to be limited to the particular drug delivery device 1 described herein below although it may be particularly advantageous for this device.

The drug delivery device 1 comprises a cartridge 2. Within the cartridge a drug 3, which may be a liquid drug, is retained. Furthermore, a bung 4 is movably retained in the cartridge 2. The bung 4 seals the cartridge 2 proximally to prevent drug 3 from dripping out of the cartridge 2. If the bung 4 is driven in the distal direction with respect to the cartridge, drug may be dispensed from the cartridge through an outlet 5 of the cartridge, provided that fluid communication between the interior of the cartridge and the exterior is provided, for example by means of a needle unit which pierces membrane 6 which seals the outlet 5.

"Distal" as used herein refers to the direction or the end of an element facing the dispensing end of the drug delivery device and "proximal" as used herein refers to the direction or the end of an element facing away from the dispensing end of the drug delivery device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The drug delivery device 1 further comprises a drive mechanism which is arranged and operable to drive movement of the bung in the distal direction with respect to the cartridge to dispense drug 3 from the device. The device 1 described herein is similar to the one described in WO 2008/058665 A1, the disclosure content of which is incorporated by reference herewith into the present application as far as the design of the device and, in particular, of its drive mechanism, is concerned. Elements of the drive mechanism may be housed in a body 7 of the drug delivery device 1. The cartridge may be connected to the body 7, either directly or, as depicted, by means of a cartridge retainer or cartridge holder 8. The cartridge holder 8 may be, releasably or permanently, coupled to the body 7.

The drug delivery device further comprises a cap 9. The cap 9 is releasably attachable to the body. The cap 9 is suitable to cover the dispensing end of the drug delivery device 1, preferably the cartridge 2 or the cartridge holder 8. For preparing the device for drug delivery, the cap may be removed and a needle unit may be attached to the outlet to provide fluid communication between the interior of the cartridge 2 and the outside.

The drug delivery device 1 further comprises a piston rod 10 which is arranged to transfer a driving force to the bung 4. The piston rod 10 comprises a main body 14. The piston rod 10, in the present case a lead screw, may be threadedly engaged with a nut member 11. The nut member 11 is expediently axially and rotationally secured within the body 7. Thus, if the piston rod 10 is rotated, on account of its threaded engagement with the nut member, it is displaced axially with respect to the body and, consequently, advanced within the cartridge 2 to dispense drug 3 from the cartridge 2.

The piston rod 10, particularly the main body 14, is provided with a piston rod thread 12. By means of the thread 12, the threaded engagement between piston rod 10 and nut member 11 can be established. The piston rod thread 12 is arranged in a distal section of the main body 14.

Figure 2:
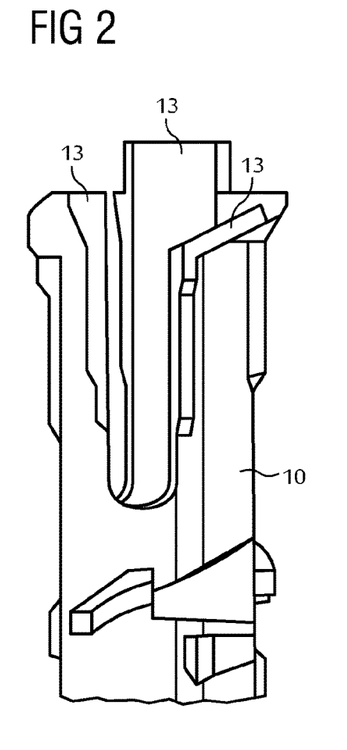
FIG. 2 shows a section of a first member with the elastically displaceable features on the basis of a plane view.

In a proximal section of the piston rod 10, one or more of elastically displaceable features 13 are arranged. The elastically displaceable features 13 are elastically deformable and may be formed integrally with the main body 14 of the piston rod 10, for example. The elastically displaceable features 13 may alternatively be resiliently mounted to the main body 14. However, with respect to manufacturing costs, an integral formation is expedient. The main body 14 is expediently rigid, whereas the features 13 are flexible, on account of cut-outs in the main body 14. The features 13 extend axially. The features 13 can be embodied as axially extending fingers.

The main body 14 further defines a hollow interior 15 wherein components of the device or of the piston rod 10 can be arranged. The piston rod may be a multi-part component.

The drug delivery device 1 comprises a drive member 16. The drive member may be a drive sleeve. The drive member 16 may be designed to transfer a driving force from the user to the piston rod 10. For this purpose, the drive member 16 may be movable in the proximal direction with respect to the body 7 for setting a dose and in the distal direction for delivering the dose. The distal movement may be transferred or converted into movement of the piston rod. During the proximal movement, the piston rod 10 is expediently stationary. The drive member 16 may be rotationally secured to the body such that no relative rotation may be allowed. The piston rod 10, in particular the proximal section with the elastically displaceable features is retained in and preferably in contact with the drive member 16.

The device further comprises a dose member 17. The dose member 17 is operable by a user and movable with respect to the body 7 in the proximal direction to set a dose and in the distal direction for delivering the set dose. The dose member is rotationally and axially locked to the drive member, i.e. axial movement of the dose member with respect to the body is permitted, whereas rotational relative movement is prevented. Alternatively, drive member 16 and dose member 17 can be formed unitarily.

Figure 3:
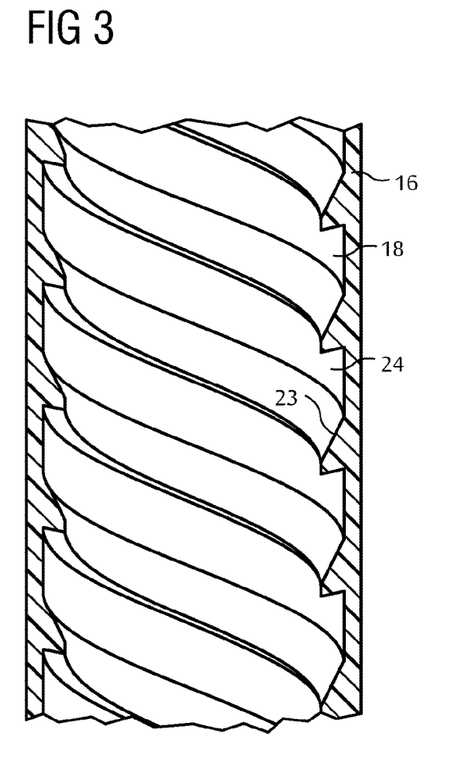
FIG. 3 shows, on the basis of a schematic sectional view, a section of a second member.

The drive member 16 comprises a drive member thread 18. The drive member thread may be a female thread and/or a helical thread. The drive member thread 18 is disposed along an inner surface of the drive member 1. The drive member thread 18 may be defined by a protrusion 23, which preferably extends along the interior of the drive member 16. The drive member thread 18 is arranged to interact with the elastically displaceable features 13 during operation of the device 1. The protrusion 23 is arranged to interact with the elastically displaceable features 13 during operation of the device 1.

FIG. 1 shows a drug delivery device 1 with a full cartridge 2, i.e. no dose has been delivered yet. As doses of drug are delivered from the cartridge 2 the piston rod 10 is successively moved distally with respect to the drive member 16.

During dose setting, the piston rod 10 is axially and rotationally secured such that when the drive member 16 is moved proximally into a dose set position. During this movement of the drive member 16 the elastically displaceable features 13 of the piston rod 10 are deflected radially inwardly and slide out of engagement with the drive member thread 18 and are thus displaced relative to the main body 14. The deflection is achieved by the section of the protrusion 23 defining the drive member thread 18, while the section abuts the respective elastically displaceable feature 13. The dose setting travel of the drive member 16 just exceeds the length of one pitch of the drive member thread 18. Thus, in the dose set position, the elastically displaceable features of the piston rod 10 re-engage with the drive member thread 18 as they move back towards the undisplaced position on account of the elastic restoring force. The movement towards the undisplaced position may be stopped when the respective elastically displaceable feature hits the drive member 16 and provides an audible and/or tactile feedback that the dose has been set. For dispensing the dose, the drive member is moved in the distal direction with respect to the body 7 towards the position it had before the setting action was performed, i.e. towards the position depicted in FIG. 1. During the dispensing action, the drive member thread 18 is used to rotate the piston rod 10. Particularly, distal facing surfaces of the protrusion 23, engage proximally facing surfaces of the elastically displaceable features 13. Thus, during dose delivery, no elastic displacement of the features 13 is caused, but the piston rod 10 is rotated and thus advanced through the nut member 11. The elastically displaceable features are used to create feedback during dose setting and to drive movement of the piston rod during dose dispensing.

Figure 4:
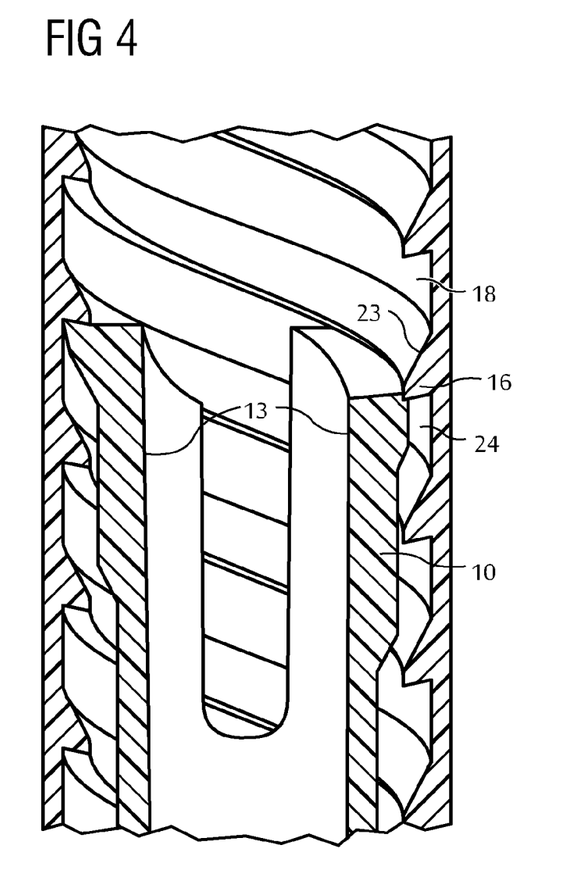
FIG. 4 shows, on the basis of a schematic sectional view, an exemplary embodiment of an assembly comprising the first member and the second member of FIGS. 2 and 3.

FIG. 4 shows a situation near the end of a dose setting operation where the right elastically displaceable feature 13 is still radially inwardly displaced by a section of the protrusion 23, i.e. a position shortly before the dose setting action has been completed and before the feature 13 engages the space 24, i.e. the next winding of the thread 18. FIG. 2 shows the proximal section of the piston rod 10 and FIG. 3 shows a section of the drive member 16.

During dose delivery, the drive member 16 is moved distally with respect to the body 7 and the elastically displaceable features 13, particularly a proximally facing surface thereof, interact with the drive member thread 18, particularly a distal facing surface of the protrusion defining the thread, such that, as the drive member 16 is rotationally locked to the body 7, the piston rod 10 is caused to rotate and, on account of the threaded engagement with the nut member 11, caused to advance in the distal direction with respect to the body 7. Consequently, the drive member thread 18 is designed as a non self-locking thread which causes the piston rod to rotate when it is subject to an axial load. The threads 18 of the drive member and 12 of the piston rod may have opposite hands. During dose delivery the piston rod 10 is advanced by a distance that corresponds to the relationship between the leads of the piston rod thread 12 and the drive member thread 18 which, of course, may be different. The piston rod thread 12 lead is less than the one of the drive member thread 18. The mechanical advantage may be 3.2:1 or, if some lost motion of the drive member is accounted for which does not drive the piston rod 10, 4:1.

The piston rod 10 further comprises an adjusting member 19. The adjusting member is retained within the interior 15 of the main body 14. The adjusting member 19 is threadedly engaged with the main body 14 of the piston rod 10, particularly with a thread in the region of the distal end of the main body. By means of the adjusting member 19 a length of the piston rod 10 can be varied. A distal end of the adjusting member may be provided with a bearing member 20 which is designed to abut the bung 4 to advance the bung when the piston rod 10 is moved distally. The threaded engagement between the adjusting member 19 and the main body 14 can be designed such that it is a self-locking, i.e. no relative rotation occurs when the adjusting member 19 or the main body 14 is subject to an axial load. Accordingly, it is avoided that the adjusting member 19 rotates with respect to the main body 14 when the piston rod advances axially. By means of the adjusting member the length of the piston rod can be varied. Consequently, a gap between the piston rod and the bung which gap could be present if the piston rod had a fixed length during the assembling of the device may be reduced or even eliminated by varying the length of the piston rod 10 by means of the adjusting member 19. Thus, already the first dose of drug delivered form a new cartridge by the drug delivery device 1 can be used by the user and no priming or prime shot is necessary to remove tolerances in the drug delivery device.

The adjusting member 19 may be rotationally locked with respect to a locking member 21. Locking member 21 may be retained within the main body 14 of the piston rod 10. The locking member 21 may be used during assembly of the device to rotate the adjusting member and thus to vary the length of the piston rod 10. The locking member may be accessible from the proximal end of the piston rod 10 during assembly, e.g. before the dose member is secured to the drive member. Once the desired length of the piston rod has been reached, the locking member 21 may be moved axially with respect to the main body 14 and the adjusting member 19 and, during this movement, be rotationally secured with respect to the main body 14 and also axially secured against movement in the proximal and/or distal direction, for example by a snap-fit engagement, with respect to the adjusting member 19. The rotational locking between the locking member 21 and the main body 14 may be achieved by splines provided on the locking member and slots on an interior surface of the main body in a section of the main body, the splines engaging the slots when the locking member 21 is moved distally with respect to the main body 14.

The device depicted in FIG. 1 is fully operable to set and dispense doses of the drug 3. In addition to the components of the drug delivery device, the drug delivery device comprises an attenuation member 22 which, on its own, is not necessary for the drug delivery device 1 to function appropriately.

In the following text, the operation of the attenuation member is described in conjunction with the piston rod 10 as a first member and the drive member 16 as a second member. However, it should be appreciated that the attenuation member could also be used for other elements in other devices to influence the force for displacing features of these elements and/or feedbacks generated by these elements.

The attenuation member 22 is retained within the piston rod. Particularly, the attenuation member 22 may be clamped between the elastically displaceable features 13. For this purpose, the attenuation member 22 may be chosen so as to have a diameter slightly greater than the one of the free space defined between the elastically displaceable features in the position they have when the piston rod is not provided with the attenuation member 22. If the attenuation member 22 is then inserted, the elastically displaceable features are slightly displaced outwardly. The elastic restoring force is therefore inwardly directed and clamps the attenuation member 22 to the piston rod 10, thereby securing the attenuation member 22 to the piston rod 10. The attenuation member 22 may be made of a rubber, for example. The attenuation member 22 has a piston-like shape. The attenuation member 22 is expediently elastically deformable.

The attenuation member 22 can be used to tune the force required to elastically displace the elastically displaceable features 13 and/or the audible or tactile feedback generated during operation of the device. In addition to the force required to displace the elastically displaceable features 13 inwardly, which would have to be exerted without the attenuation member 22, in the depicted drug delivery device with the attenuation member the force which is required to deform the attenuation member 22 has to be exerted. Thus, the force required to displace the displaceable features 13 is effectively increased. This can be used to customize the device to various users and, particularly their needs or physical conditions.

The attenuation member 22 can be used to influence the sound and/or the volume of audible feedbacks and/or the feeling of the tactile feedback experienced by the user during operation of the drug delivery device, such as feedbacks that the dose has been set in the device described further above. In other devices, the attenuation member may be used to tune the feedback generated when the dose has been dispensed or the feedback generated during the dispensing action to signal to a user that the device functions correctly.

Expediently, the restoring force which tends to restore the shape of the attenuation member 22 after it was deformed by displacing the elastic displacement of the features 13 to the displaced position is greater than the restoring force which tends to move the features 13 to the undisplaced position. In this way, permanent contact of the attenuation member and of the features 13 can be kept during the movement towards the undisplaced position.

Further, as the force required to displace the elastically displaceable features is increased, the attenuation member can absorb external forces, such as vibrations, for example if the drug delivery device falls on the floor inadvertently. Thereby, the likelihood of a malfunction of the device is reduced.

Still further, the attenuation member 22 delimits the interior 15 of the main body 14 of the piston rod 10 such that it is ensured that elements retained therein may not move and fall out of the main body through that end of the interior 15 which is closed by the attenuation member 22. For example, the attenuation member 22 may be in mechanical cooperation, preferably abutment, with the locking member 21 and/or the adjusting member 19. Consequently, it is further ensured that the piston rod 10 stays reliably assembled by means of the attenuation member 22.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

The invention claimed is:

1. An assembly for a drug delivery device, comprising:
a first member comprising a main body and an elastically displaceable feature connected to the main body;
a second member comprising a protruding feature, wherein the protruding feature is arranged to mechanically cooperate with the elastically displaceable feature of the first member to elastically displace the elastically displaceable feature of the first member when the first member is moved with respect to the second member or when the second member is moved with respect to the first member; and
an attenuation member received within an interior of the first member, wherein the attenuation member mechanically cooperates with the elastically displaceable feature of the first member to influence a force required to be exerted on the elastically displaceable feature of the first member to displace the elastically displaceable feature of the first member elastically with respect to the main body; and
wherein the elastically displaceable feature of the first member is arranged to be displaced in a radial direction when the first member is moved axially with respect to the second member or when the second member is moved axially with respect to the first member.

2. The assembly according to claim 1, wherein the attenuation member is elastically deformable and is configured to be elastically deformed when the elastically displaceable feature of the first member is displaced, and wherein the attenuation member is configured such that an elastic restoring force required to restore the attenuation member to an undeformed shape is greater than an elastic restoring force provided by elastic displacement of the elastically displaceable feature of the first member.

3. The assembly according to claim 1, wherein the assembly comprises a plurality of elastically displaceable features comprising the elastically displaceable feature of the first member and the attenuation member is clamped between at least two of the elastically displaceable features.

4. The assembly according to claim 1, wherein the first member is a piston rod.

5. The assembly according to claim 1, wherein the first member comprises a first section configured to establish a threaded engagement of a first lead, the elastically displaceable feature of the first member being arranged in the first section and being provided to establish the threaded engagement.

6. The assembly according to claim 5, wherein the first member comprises a second section provided to establish a threaded engagement of a second lead which is different from the first lead.

7. The assembly according to claim 1, wherein the elastically displaceable feature of the first member is elastically deformable.

8. A drug delivery device, the drug delivery device comprising a feedback mechanism, the feedback mechanism comprising an assembly, the assembly comprising:
a first member comprising a main body and an elastically displaceable feature connected to the main body;
a second member comprising a protruding feature, wherein the protruding feature is arranged to mechanically cooperate with the elastically displaceable feature of the first member to elastically displace the elastically displaceable feature of the first member when the first member is moved with respect to the second member or when the second member is moved with respect to the first member; and
an attenuation member, wherein the attenuation member mechanically cooperates with the elastically displaceable feature of the first member to influence a force required to be exerted on the elastically displaceable feature of the first member to displace the elastically displaceable feature of the first member elastically with respect to the main body
wherein the attenuation member is provided to adjust a user feedback generated by the elastically displaceable feature of the first member, the user feedback comprising at least one of an audible feedback and a tactile feedback, and the elastically displaceable feature of the first member being configured to generate the user feedback when the elastically displaceable feature of the first member, after having been displaced, moves towards its undisplaced position; and
wherein the elastically displaceable feature of the first member is arranged to be displaced in a radial direction when the first member is moved axially with respect to the second member or when the second member is moved axially with respect to the first member.

9. The drug delivery device of claim 8, wherein the elastically displaceable feature of the first member is configured to generate the user feedback during dose setting, during dose dispensing, or at the end of the dose dispensing.

10. A drug delivery device comprising an assembly, the assembly comprising:
a first member, the first member being a piston rod comprising a main body and an elastically displaceable feature connected to the main body;
a second member comprising a protruding feature, wherein the protruding feature is arranged to mechanically cooperate with the elastically displaceable feature of the piston rod to elastically displace the elastically displaceable feature of the piston rod when the piston rod is moved with respect to the second member or when the second member is moved with respect to the piston rod; and
an attenuation member received within an interior of the piston rod,
wherein the attenuation member mechanically cooperates with the elastically displaceable feature of the piston rod to influence a force required to be exerted on the elastically displaceable feature of the piston rod to displace the elastically displaceable feature of the piston rod elastically with respect to the main body,
wherein the elastically displaceable feature of the piston rod is arranged to be displaced elastically from an undisplaced position to a displaced position during operation of the drug delivery device; and
wherein the elastically displaced feature of the piston rod is arranged to be displaced in a radial direction when the piston rod is moved axially with respect to the second member or when the second member is moved axially with respect to the piston rod.

11. The drug delivery device according to claim 10, wherein the second member is a drive member movable to deliver a dose of a medicament.

12. The drug delivery device according to claim 10, wherein the piston rod comprises a plurality of elastically displaceable features comprising the elastically displaceable feature of the piston rod and wherein the attenuation member is retained within the piston rod and clamped between the elastically displaceable features of the piston rod.

13. A method of operating a drug delivery device, the drug delivery device comprising an assembly, the assembly comprising:
 a first member comprising a main body and an elastically displaceable feature connected to the main body;
 a second member comprising a protruding feature, wherein the protruding feature is arranged to mechanically cooperate with the elastically displaceable feature of the first member to elastically displace the elastically displaceable feature of the first member when the first member is moved with respect to the second member or when the second member is moved with respect to the first member; and
 an attenuation member received within an interior of the first member, wherein the attenuation member mechanically cooperates with the elastically displaceable feature of the first member to influence a force required to be exerted on the elastically displaceable feature of the first member to displace the elastically displaceable feature of the first member elastically with respect to the main body; and
 wherein the elastically displaceable feature of the first member is arranged to be displaced in a radial direction when the first member is moved axially with respect to the second member or when the second member is moved axially with respect to the first member;
 the method comprising:
 using the attenuation member of the assembly to tune a force required to elastically displace the elastically displaceable feature of the first member by bringing the attenuation member into mechanical cooperation with the elastically displaceable feature of the first member.

14. The method according to claim 13, further comprising:
 applying the force to elastically displace the elastically displaceable feature of the first member; and
 releasing the force to move the elastically displaceable feature of the first member to an undisplaced position to generate a user feedback, the user feedback comprising at least one of an audible feedback and a tactile feedback.

15. The method according to claim 14, wherein applying the force to elastically displace the elastically displaceable feature of the first member comprises at least one of displacing the second member relative to the first member or displacing the second member relative to the first member such that the second member mechanically cooperates with the elastically displaceable feature of the first member.

16. The assembly according to claim 1, wherein the elastically displaceable feature of the first member comprises a flexible finger extending axially with respect to the main body.

17. An assembly for a drug delivery device, comprising:
 a first member comprising a main body and an elastically displaceable feature connected to the main body;
 a second member comprising a protruding feature, wherein the protruding feature is arranged to mechanically cooperate with the elastically displaceable feature of the first member to elastically displace the elastically displaceable feature of the first member when the first member is moved with respect to the second member or when the second member is moved with respect to the first member; and
 an attenuation member received within an interior of the first member, wherein the attenuation member mechanically cooperates with the elastically displaceable feature of the first member to influence a force required to be exerted on the elastically displaceable feature of the first member to displace the elastically displaceable feature of the first member elastically with respect to the main body;
 wherein the protruding feature is a thread or a section of a thread; and
 wherein the second member is at least one of:
  designed to transfer a driving force to the first member by mechanical cooperation of the protruding feature and the elastically displaceable feature of the first member; or
  a drive sleeve, wherein the elastically displaceable feature of the first member is retained in the drive sleeve and in mechanical contact with an inner surface of the drive sleeve.

18. An assembly for a drug delivery device, comprising:
 a first member comprising a main body and an elastically displaceable feature connected to the main body, wherein the first member further comprises a first section configured to establish a threaded engagement of a first lead, the elastically displaceable feature of the first member being arranged in the first section and being provided to establish the threaded engagement; and
 an attenuation member received within an interior of the first member, wherein the attenuation member mechanically cooperates with the elastically displaceable feature of the first member to influence a force required to be exerted on the elastically displaceable feature of the first member to displace the elastically displaceable feature of the first member elastically with respect to the main body.

19. A drug delivery device comprising the assembly of claim 1 and a drug.

* * * * *

UNITED STATES PATENT AND TRADEMARK OFFICE
CERTIFICATE OF CORRECTION

PATENT NO. : 10,420,890 B2
APPLICATION NO. : 14/913188
DATED : September 24, 2019
INVENTOR(S) : Michael Jugl and Axel Teucher

It is certified that error appears in the above-identified patent and that said Letters Patent is hereby corrected as shown below:

In the Claims

Column 15, Line 46, Claim 3, delete "features" and insert -- features, --.

Column 17, Line 6, Claim 12, delete "features" and insert -- features, --.

Signed and Sealed this
Twenty-fourth Day of December, 2019

Andrei Iancu
*Director of the United States Patent and Trademark Office*